(12) United States Patent
Zhou et al.

(10) Patent No.: US 6,944,204 B2
(45) Date of Patent: Sep. 13, 2005

(54) LASER-INDUCED BREAKDOWN SPECTROSCOPY WITH SECOND HARMONIC GUIDE LIGHT

(75) Inventors: Wang Long Zhou, Reading, MA (US); Yongwu Yang, Belmont, MA (US); Victor S. Sapirstein, Pound Ridge, NY (US); Shaoqing Peng, Newton, MA (US)

(73) Assignee: Lambda Solutions, Inc., Pound Ridge, NY (US)

( * ) Notice: Subject to any disclaimer, the term of this patent is extended or adjusted under 35 U.S.C. 154(b) by 0 days.

(21) Appl. No.: 10/766,373

(22) Filed: Jan. 28, 2004

(65) Prior Publication Data

US 2004/0183018 A1 Sep. 23, 2004

Related U.S. Application Data

(60) Provisional application No. 60/443,465, filed on Jan. 29, 2003.

(51) Int. Cl.[7] ............................. H01S 3/00; G01J 3/00; G01J 3/28
(52) U.S. Cl. ....................... 372/109; 356/300; 356/326; 356/451
(58) Field of Search ........................ 372/109; 356/300, 356/326, 451

(56) References Cited

U.S. PATENT DOCUMENTS

| | | | | |
|---|---|---|---|---|
| 3,941,478 A | * | 3/1976 | Dougherty et al. | 356/30 |
| 5,294,289 A | * | 3/1994 | Heinz et al. | 216/60 |
| 5,392,124 A | * | 2/1995 | Barbee et al. | 356/632 |
| 6,762,835 B2 | * | 7/2004 | Zhang et al. | 356/318 |
| 6,785,471 B2 | * | 8/2004 | Lee et al. | 398/25 |

* cited by examiner

*Primary Examiner*—Don Wong
*Assistant Examiner*—Leith Al-Nazer
(74) *Attorney, Agent, or Firm*—Silla Cummis Esptein & Gross PC

(57) ABSTRACT

A laser system comprising a laser for providing a laser beam, a non-linear optical crystal in the laser beam path creating a second order light, a laser beam expander in the beam path after the non-linear crystal, a dichromatic mirror in the beam path after the beam expander, an objective lens that focuses the laser beam on a sample and collects transmission from the sample before the sample transmission impacts the dichromatic mirror, a partial reflector of the second order light in the transmission path after the dichromatic mirror, and a coupler for coupling an optical component to the sample transmission.

19 Claims, 3 Drawing Sheets

LASER-INDUCED BREAKDOWN SPECTROSCOPY WITH SECOND HARMONIC GUIDE LIGHT

CROSS REFERENCE TO RELATED APPLICATIONS

The present application claims benefit of U.S. Provisional Application No. 60/443,465 filed Jan. 29, 2003.

FIELD OF INVENTION

The present invention is related to laser guiding and calibration and specifically related to the field of laser induced breakdown spectroscopy and detection.

BACKGROUND OF THE INVENTION

Laser-induced breakdown spectroscopy (LIBS) is an elemental analysis technique that detects the atomic emissions from a plasma. The plasma is formed by focusing a high energy laser pulse on a sample. LIBS provides for real time and in-situ measuring of the elemental composition of samples of interest. In a LIBS system, a short pulse (~ns) laser beam is tightly focused on a sample.

A typical laser used is a pulsed (50 to 100 mJ), high power, near-IR laser, such as Nd:YAG, Nd:YVO$_4$, and Nd:YLF lasers. The high intensity laser spot that is formed heats, vaporizes, atomizes and ionizes the constituent elements of the sample within a small volume (<0.1 mm$^3$) by forming a high temperature plasma or spark. Since the temperature in the plasma is typically around 10,000 K, the ablated atoms are ultimately electronically excited.

As the ions relax, they emit radiation at characteristic wavelengths. The characteristic spectrum typically ranges from the ultraviolet to near-infrared. The intensities of the emission lines emitted when the plasma decays are analyzed using a spectrometer. This signal radiation is weak in comparison to the plasma-inducing laser pulse, so a highly sensitive, gated detector is commonly used with a filter to eliminate the laser light. The detector is typically either a charge-coupled-device array, or a camera. These intensities can provide quantitative and qualitative information regarding the sample.

Use of LIBS techniques has grown due to the development of new laser sources and instrumentation. In addition, low-cost spectrometers with high spectral coverage and resolution have opened up new applications. Other advantages afforded by LIBS include the lack of any required sample preparation, results are obtained in near real time, and remote analysis is possible. Optical endoscopes or fiber optic cables provide in situ analysis of materials in remote or hazardous environments.

There are still many problems associated with LIBS systems. Whereas qualitative analysis has been widely demonstrated for a range of samples, quantitative measurements are more affected by the substrate properties. The temperature reached after the laser pulse and the electron density are fundamental parameters of plasma formation processes and dynamics and are directly dependant on the laser/sample interaction at a given wavelength. One important parameter relating to plasma dynamics is the decay time, which is strictly related the selection of the detection window chosen in which local thermodynamic equilibrium can be assumed to hold. Another difficulty is plasma expansion, which is not well understood. To breakdown the chemical elements of a sample, the surface area ablated by the laser pulse and the shockwave must be small. The laser spot intensity focused on the sample must exceed a certain threshold to form a plasma. Tight and optimum focusing is crucial in a LIBS system for reaching the intensity threshold required. At the same time, it is desirable to keep the total laser power as low as possible while still exceeding the intensity threshold. Using a laser of lower power not only decreases system cost but also reduces the possibility of damaging the sample.

In prior-art LIBS systems, a visible guide light beam from a separated light source such as low-power HeNe laser is employed for laser focusing and target identification. Both focusing and target identification require this visible guide light being well aligned with the high-power near-IR laser beam. Obviously, such an arrangement complicates LIBS systems since it requires an extra light source, more optics and cumbersome alignment.

Also, the typical LIBS system, especially one with portability requires frequent wavelength calibration due to mechanical factors such as vibration and heating.

One second order nonlinear optical process is that of second harmonic generation The second harmonic is generated by passing a beam with angular frequency $\omega_1 = 2\pi v$ through a crystal having a nonzero value of Xz such that the output beam emerging from the crystal contains both the frequency of the fundamental wave and twice the frequency of the fundamental wave. From the photon perspective, the energy levels of the photons of the fundamental frequency combine to produce twice the energy level. These levels do not accrue population since they are not eigenstates of the material. Instead, the photons are destroyed and simultaneously recreated as a single photon of twice the frequency.

SUMMARY OF THE INVENTION

The present invention uses the second harmonic of the fundamental laser beam as a guide and reference beam. The second harmonic of the near-IR spectrum ("NIR") is in the visible range. Therefore, the second harmonic output beam is visible. The generation of the second harmonic is simple and convenient, particularly for a high power pulsed laser. Also, the second harmonic travels in a direction almost entirely overlapped with that of the fundamental laser beam so no further alignment is necessary. Therefore, the preferred embodiment of the present invention provides the second harmonic of a NIR laser.

The second harmonic visible light of the present invention can also be used to illuminate the laser-induced breakdown process so that it can be monitored, imaged, and displayed. The second harmonic light can also be an absolute wavelength marker for a LIBS spectrometer, which typically requires timely calibration. Such calibration could be costly and time consuming. An all-time and in-situ wavelength marker will tell when such a calibration should be carried out. Furthermore, a second wavelength marker could be added through third-harmonic generation so that wavelength calibration could be done in real time and automatically.

In addition, since the power of the second harmonic is directly related to the fundamental wave power, it can also be used to monitor the LIBS laser power yielding a basis for quantitation of constituents in examined samples. The fundamental and, in the case when the doubling crystal is in the path of the laser, the second harmonic are directed to the sample by a dichroic mirror. The mirror is chosen so that a percentage of the second harmonic passes through, directed to the detector to provide single pixel wavelength calibration. The magnitude of the signal at this pixel is in a direct relationship to the power of the fundamental.

The present invention provides an LIBS system comprising a near-IR pulse laser, a spectrometer, and a frequency doubling crystal for generating a visible laser as a guide and reference light.

Another object of the present invention is to provide an LIBS system comprising a near-IR pulse laser, a spectrometer, a frequency doubling crystal for generating a visible laser as a guide and reference light, and a means for monitoring, imaging, or displaying the laser-induced breakdown process.

A further object of the present invention is to provide an LIBS system having two absolute wavelength markers for real-time and automatic wavelength calibration. The two wavelength markers are produced by frequency doubling and tripling, respectively.

DETAILED DESCRIPTION OF THE DRAWINGS

Figure 1:
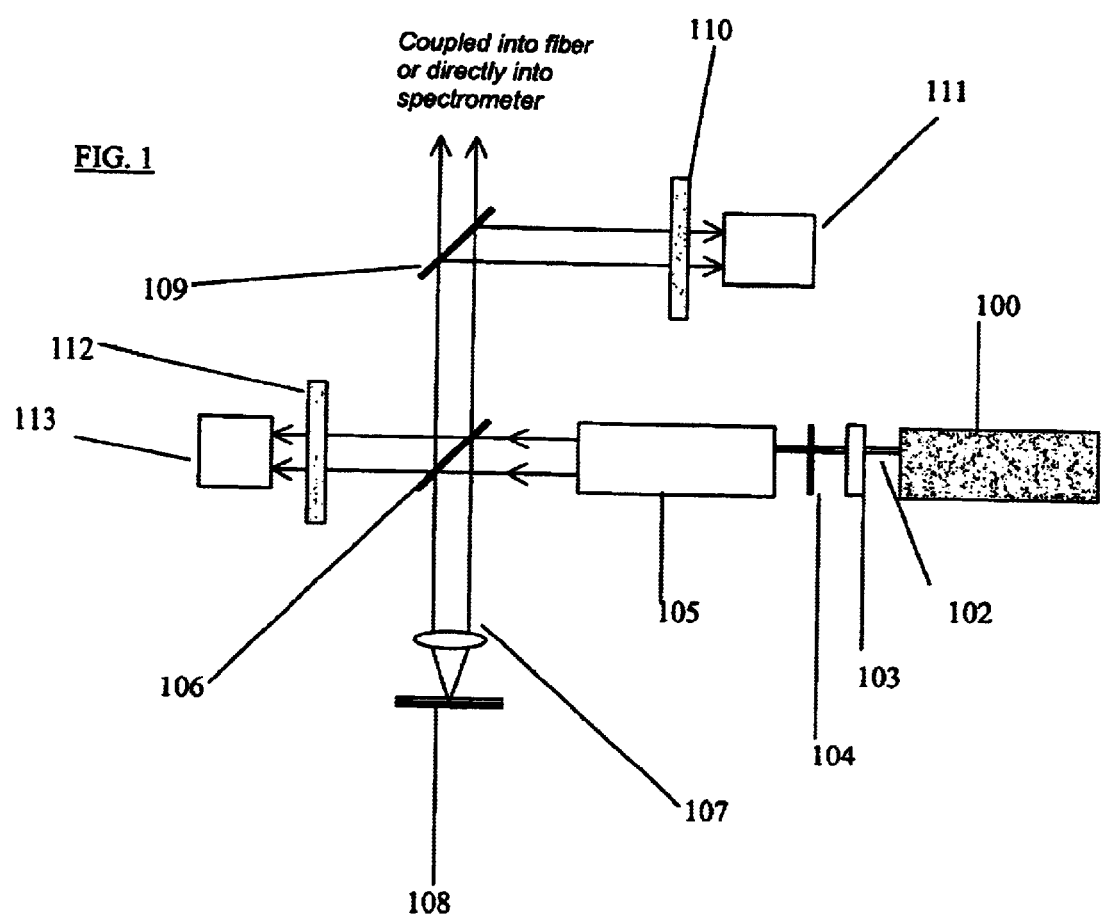
FIG. 1 is a schematic representation of an embodiment of the present invention.

The laser 100 of FIG. 1 preferably emits a high-power, near-IR pulse laser beam 102. Preferable examples of this include Nd:YAG, Nd:YVO$_4$, and Nd:YLF lasers such as a 1064 nm YAG laser pulsed customarily at between 10 to 50 Hz with 1 mJ to 1 J and preferably between 50 to 100 mJ energy per pulse output. This is sufficient power in lasers with narrow pulse widths, i.e., below 1(one) nanosecond. The beam 102 travels through a nonlinear optical crystal 103, such as potassium titanyl phosphate or KTiOPO$_4$ (KTP), Lithium triborate or LiB$_3$O$_5$ (LBO), Beta-Barium Borate or βBaB$_2$O$_4$ (BBO), Potassium Dihydrogen Phosphate (KDP) and Potassium Dideuterium Phosphate (KD*P). Other possibilities include but are not limited to Potassium Titanyl Phosphate (KTP), Lithium Niobate (LiNbO$_3$), Magnesium Oxide Doped Lithium Niobate Crystals (MgO:LiNbO$_3$), and KN (KNbO$_3$) which is a peovskite-type crystal. Preferably, the crystal 103 is cut, polished, and coated for frequency doubling of the fundamental laser wavelength. It is preferred that the frequency-doubled light (second harmonic) should be in the visible region i.e., within 400 nm~700 nm, and most preferably in the most human-sensitive green region (490~560 nm). For example, the invention can use a pulsed YAG laser at 1064 nm (the fundamental), which would produce a second harmonic at 532 nm in the visible green region.

Figure 3:
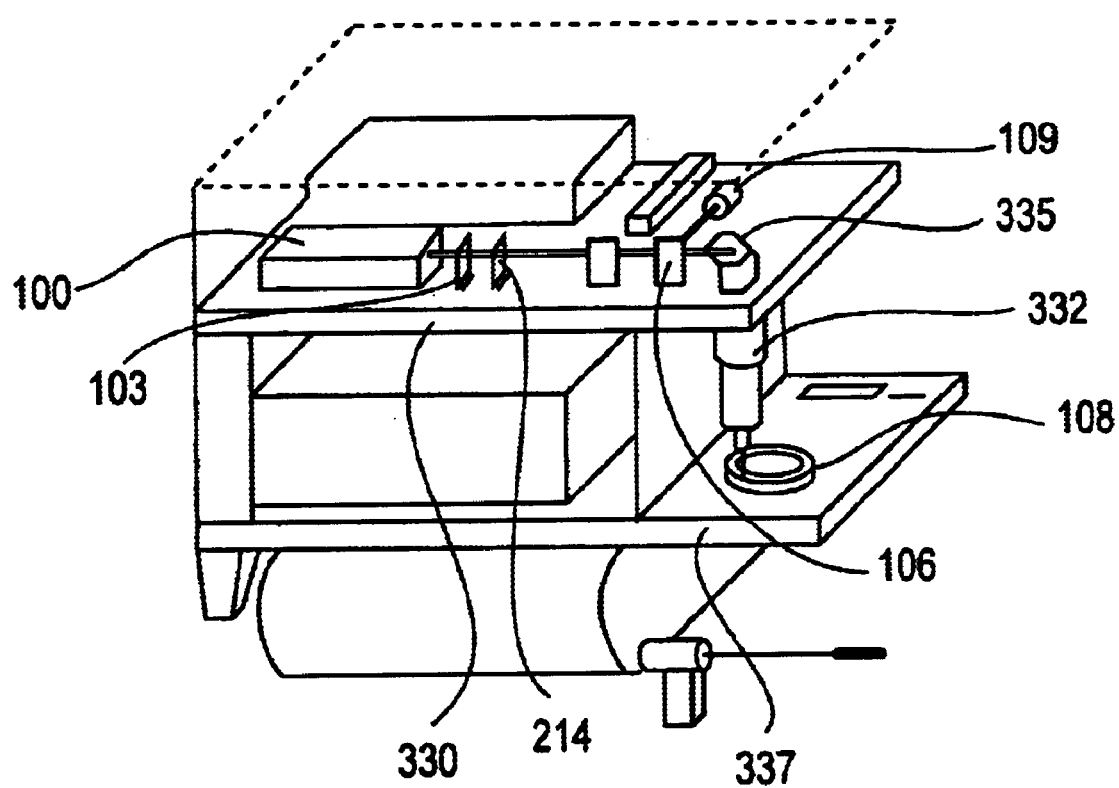
FIG. 3 is a proportional view of an embodiment of the present invention.

A shown in FIG. 3, the non-linear optical crystal 103 is preferably mounted on a removable stage 330 or housing. This provides for, among other things, removing the crystal 103 from the optical path if the green light affects measurement, e.g., the green wavelength overlaps with a fluorescence peak.

Figure 2:
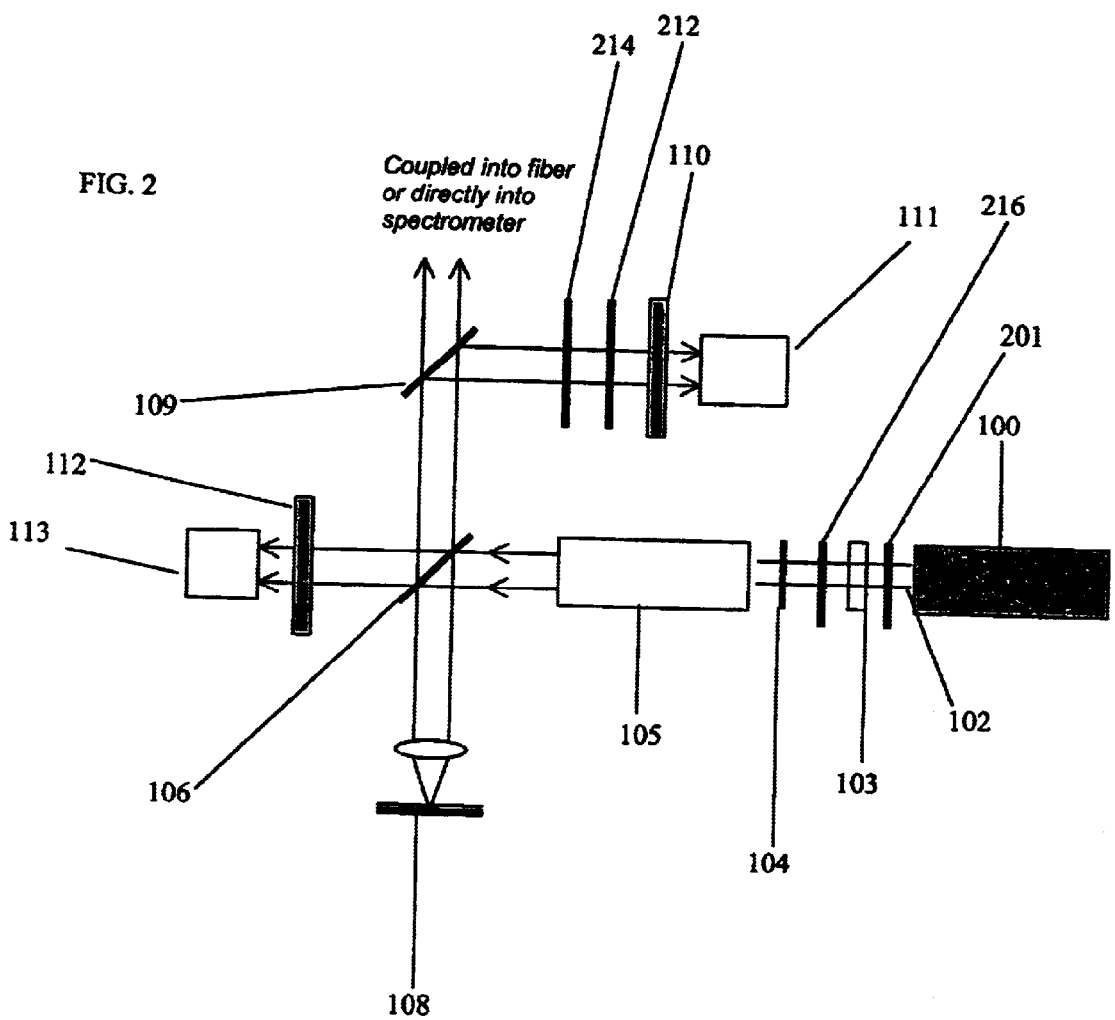
FIG. 2 is a schematic representation of a second embodiment of the present invention.

A fundamental laser shutter 104 is used to control the number of laser pulses of the fundamental wavelength passing through the system. The shutter 104 is typically a manual shutter and is preferably made of a dichromatic mirror. It only shuts off the fundamental wavelength when in the closed position. In the embodiment of FIG. 2, a second shutter 201 can be placed in the front of the laser 100 to block the fundamental and second harmonic light if necessary.

A beam expander 105 expands the beam 102. The beam expander 105 has an expansion ratio of preferably 2x to 5x.

The beam expander 105 is to reduce the divergence angle of the beam 102 containing both the fundamental and second harmonic wavelengths and thereby make the focused beam diameter smaller. The fundamental portion of the beam is then totally reflected by the dichromatic mirror 106 and focused on the sample material 108 by an objective lens 107. In the example being used, the dichromatic mirror preferably has a high reflection at laser wavelength 1064 nm and high transmission at broad fluorescence range of 300 to 900 nm.

The objective lens 107 is preferably housed in a housing 332 shown in FIG. 3. In FIG. 3, a prism or lens 335 helps direct the beam appropriately. The sample 108 is set on a movable sample stage 337.

A plasma is created at the spot upon which the fundamental beam is focused. The atomic fluorescence created by the relaxation of the plasma is collected by the objective lens 107 and transmitted by the dichromatic mirror 106 and the partial reflector of the second harmonic guide light 109 and coupled into a fiber optic bundle or directly into a spectrometer for analysis. The objective lens 107 serves as a focusing lens of the laser beam 102 and a collecting lens of the atomic fluorescence from the sample 108.

A small portion (preferably less than 10%) of the second harmonic light is also reflected by the dichromatic mirror 106 and also focused by the lens 107 on the sample 108. The second harmonic light is then scattered back by the sample 108 and collimated by the lens 107. This light is then transmitted through the dichromatic mirror 106 and partially reflected by the partial reflector 109. The partially reflected portion of the second harmonic light travels to an attenuator plate 110 and finally a monitoring element 111.

The attenuator plate 110 controls the energy levels impacting the monitoring element 111. An attenuator module can be used to accurately set the energy transmitted. Preferably, the laser beam enters the attenuator module and impacts the attenuator plate 110 directly or alternatively (as shown in FIG. 2), a shutter 214 can be set to close or open before the attenuator plate 110 to help control the light ultimately impacting the monitoring element 111. When the laser beam hits the attenuator plate 110 some portion of the light is reflected and some is transmitted to the monitoring element 111. The ratio between transmitted and reflected light is determined by the angle of incidence of the attenuator plate 110. The attenuator plate 110 is rotated either continuously or step-wise to vary the transmitted portion. As shown in FIG. 2, a compensator plate 212 can also be used. Typically the compensator plate has an anti-reflection coating. This coating is insensitive to the angle of incidence. The compensator plate 212 can rotate simultaneously with the attenuator plate 110 to eliminate beam displacement.

The monitoring element 111 can be a camera, a CCD or CMOS detector, an eyepiece for live observing, or some other known element.

The second harmonic power generated by the crystal 103 is proportional to the crystal thickness and the square of the fundamental power. A laser used in an LIBS system has a peak power typically higher than 1 MW. For such a high peak power, a crystal with a thickness of 0.5 mm or less is enough for generating sufficient power, of which a small portion reaches the element 111. It is noted that the power degradation of the fundamental wavelength due to the frequency doubling is negligible (<1%).

Producing green light through frequency doubling requires a thin crystal of less than 0.5 mm. More importantly, the optical path of the green light substantially overlaps with the fundamental frequency and therefore acts as a guide light. The focusing spot of the green light coincides exactly with the spot at which the plasma occurs. With this visible and co-axis guide light, one is able to know the portion of the sample being analyzed. This feature is particularly desired when analyzing small, inhomogeneous, or surface-rough samples. Use of the visible green by the invention eliminates the need for a visible light from a separate source that requires cumbersome alignment with extra optical circuits and elements.

A portion of the green light is mixed with the fluorescence and also reaches the spectrometer. The green wavelength of 532 nm is substantially in the center of a typical LIBS system coverage range of 200 to 900 nm. If the wavelength fluctuation of the green light can be controlled within the wavelength resolution of the spectrometer, then this green light can be used as an absolute wavelength marker. A spectrometer used in an LIBS system normally has a resolution of around 0.2 nm. To keep the green light's wavelength fluctuation under 0.2 nm the wavelength variation of the fundamental should be less than 0.4 nm. This requirement can be fulfilled by most of the lasers suitable for LIBS.

Spectrometers normally require timely calibration that could be costly and time consuming. An inline wavelength marker will tell when such a calibration is needed. The portion of the second harmonic, at 532 nm, will be detected on the CCD detector at a specific pixel. Deviation from that pixel for this signal will be the basis for determining a state of off or non-calibration.

As mentioned above the crystal 103 in FIG. 1 could be less than 0.5 mm in thickness and therefore its functional range for temperature, angle, and wavelength is enough for keeping the process of frequency doubling stable even in a harsh environment. The green light will vary only when the fundamental power changes. Therefore, this green light can also be used to monitor the laser power fluctuation.

Preferably, most of the green light is transmitted through the mirror 106 and reaches the attenuator 112 and the power detector 113. The signal from the power detector 113 is a relative reference of the laser power and can be used for spectrum normalization so that the laser power fluctuation does not affect measurement accuracy.

A typical laser power detector is a thermopile. A temperature difference is used to create a voltage by heating material on one side of the detector by the laser and placing a heat sink on the other side. The laser energy absorbed by the material is converted to heat. With the heat absorber on one surface and the heat sink on the other, a temperature difference across the thermoelectric device is created. This temperature difference causes the thermopile to generate a voltage. The voltage is proportional to the temperature difference that, in turn, is proportional to the laser power. The detector measures this voltage to provide a laser power reading typically in watts.

The green light that is transmitted through the partial reflector 109 also eases the alignment of fluorescence coupling into optical fibers or a spectrometer. The green light is used as a targeting mechanism to help couple a fiber optic bundle or a spectrometer to the beam path.

In the embodiment of the present invention shown in FIG. 2, a second non-linear crystal 216, such as LBO, BBO, and KDP, is placed between the crystal 103 and the shutter 104. The second crystal 216 mixes the fundamental and the second harmonic and generates the third harmonic 355 nm. Automatic, instant, and real-time wavelength calibration will be possible by using both 532 nm and 355 nm as absolute wavelength markers. The deviation of the second harmonic from its original pixel defines off calibration, but two wavelengths and their respective pixels are required to recalibrate because of non-linearity. By creating a second wavelength with the third harmonic this requirement is achieved. Auto adjustment of pixels corresponding to wavelength can then be determined and made.

In FIG. 1, the optical circuit starting from the monitoring element 111, passing the attenuator 110, the partial reflector 109, the dichromatic mirror 106, the objective lens 107, and ending at the sample 108 is a microscope arrangement and may be replaced with any known microscope arrangement. Also, the sample may be mapped, point by point, by using known automatic focusing technology. Therefore, in yet another embodiment, an automatic focusing device (not shown) is used in addition to or in replacement of the monitoring element 111 to control the sample-stage movement and automatically optimize focusing.

The preferred method of the present invention comprises known methods of laser-induced breakdown spectroscopy with frequency doubling of the fundamental wavelength of a laser. By doubling the frequency of particular wavelengths, the second harmonic will be in the visible range. Frequency doubling is accomplished by passing the beam from a laser through a non-linear optical crystal.

A shutter blocks the fundamental beam while the second harmonic beam is used to focus on the sample, illuminate the sample, and align the system. After completion of guide beam focusing and system alignment, the shutter is opened so that the high-power fundamental laser beam will reach the sample and induce material breakdown.

If the intensity of the laser focused on the sample is high enough, a high-temperature and short-lived plasma is formed in the center region of the focusing spot. The material within the plasma is broken down into high-energy atoms and ions that then release photons (atomic fluorescence) when falling back to the lower energy or the ground level.

Accordingly, it should be readily appreciated that the device and method of the present invention has many practical applications. Additionally, although the preferred embodiments have been illustrated and described, it will be obvious to those skilled in the art that various modifications can be made without departing from the spirit and scope of this invention. Such modifications are to be considered as included in the following claims.

What is claimed is:

1. A laser system comprising:
   a laser for providing a laser beam;
   a non-linear optical crystal in the laser beam path creating a second order light;
   a laser beam expander in the beam path after the non-linear crystal;
   a dichromatic mirror in the beam path after the beam expander;
   an objective lens that focuses the laser beam on a sample and collects transmission from the sample before the sample transmission impacts the dichromatic mirror;
   a partial reflector of the second order light in the transmission path after the dichromatic mirror; and,
   a coupler for coupling an optical component to the sample transmission.

2. A laser system as in claim 1 wherein:
   the laser is a near IR pulsed laser.

3. A laser system as in claim 2 wherein:
   the laser is selected from the group consisting of a Nd:YAG, Nd:YVO$_4$, and Nd:YLF laser.

4. A laser system as in claim 2 wherein:
the laser is a 1064 nm YAG laser pulsed at between 10 to 50 Hz with 50 to 100 mJ of output.

5. A laser as in claim 1 wherein:
non-linear optical crystal is a frequency doubling crystal.

6. A laser system as in claim 5 wherein:
the frequency doubling crystal is selected from the group consisting of potassium titanyl phosphate, lithium triborate, beta-barium borate, potassium dihydrogen phosphate, potassium dideuterium phosphate, potassium titanyl phosphate, lithium niobate, magnesium oxide doped lithium niobate, and potassium niobate.

7. A laser system as in claim 1 wherein:
the dichromatic mirror is a high reflection mirror at NIR laser wavelengths and high transmission at broad fluorescence range.

8. A laser system as in claim 1 wherein:
the dichromatic mirror allows the second order light to pass through to a detector to provide single pixel wavelength calibration based on the magnitude of the signal of the second order light at this pixel.

9. A laser system as in claim 1 wherein:
the optical component is selected from the group consisting of an eyepiece, a camera, a CCD, a CMOS, a spectrometer, and a fiber optic cable.

10. A laser system as in claim 9 further comprising:
a second shutter for blocking the laser beam in the beam path between the laser and the optical crystal.

11. A laser system as in claim 1 wherein:
the transmission from the sample is caused by the relaxation of a plasma formed at the spot on which the laser is focused.

12. A laser system as in claim 11 further comprising:
a second non-linear crystal placed between the first optical crystal and the shutter for mixing the fundamental and the second harmonic and generating the third harmonic wavelength.

13. A laser system as in claim 1 further comprising:
a shutter for blocking the fundamental laser frequency of the beam in the beam path between the optical crystal and the beam expander.

14. A laser system as in claim 1 further comprising:
a second non-linear crystal placed between the first optical crystal and the shutter for mixing the fundamental and the second harmonic and generating the third harmonic wavelength.

15. A laser system as in claim 1 further comprising:
an attenuator module placed in the transmission path prior to an optical component comprising an attenuator plate, a compensator and a shutter for controlling the energy levels impacting the optical component.

16. A laser induced breakdown spectroscopy system comprising:
a laser for providing a laser beam;
a non-linear optical crystal in the laser beam path for creating a second order light;
a laser beam expander in the beam path after the non-linear crystal;
a dichromatic mirror in the beam path after the beam expander;
an objective lens that focuses the laser beam on a sample and collects transmission from the sample before the sample transmission impacts the dichromatic mirror;
a partial reflector of the second order light in the transmission path after the dichromatic mirror;
a coupler for coupling a first optical component to the sample transmission;
a first attenuator in the transmission path after the partial reflector and before a second optical component; and
a second attenuator in the beam path after the dichromatic mirror and before a power detector.

17. A method of aligning a laser beam on a sample comprising:
providing a fundamental laser beam;
passing the laser beam through a non-linear optical crystal creating a second order light beam;
focusing the second order light beam on a sample while blocking the fundamental beam from the sample; and
providing for the fundamental beam to impact the sample at the point of focus of the second order light beam.

18. A method of determining calibration of a laser comprising:
providing a fundamental laser beam;
passing the laser beam through a non-linear optical crystal creating a second order light beam;
focusing the second order light beam on a detector at a predetermined pixel; and
determining deviation of the second order light from the predetermined pixel for determining the state of calibration.

19. A method of determining the calibration of a laser comprising:
providing a fundamental laser beam;
passing the laser beam through a non-linear optical crystal creating a second order light beam;
passing the second order light through a second non-linear crystal mixing the fundamental and the second harmonic to creating a third order light beam;
focusing the second and third order light beams on a detector at predetermined pixels; and
determining the amount of deviation of the second order light from its predetermined pixel.

* * * * *